(12) United States Patent
Wasson

(10) Patent No.: US 10,335,548 B1
(45) Date of Patent: Jul. 2, 2019

(54) SYRINGE ASSEMBLY

(71) Applicant: Alexander J. Wasson, Tempe, AZ (US)

(72) Inventor: Alexander J. Wasson, Tempe, AZ (US)

(73) Assignee: Cinti Medical, Inc., Tempe, AZ (US)

( * ) Notice: Subject to any disclaimer, the term of this patent is extended or adjusted under 35 U.S.C. 154(b) by 57 days.

(21) Appl. No.: 15/619,082

(22) Filed: Jun. 9, 2017

(51) Int. Cl.
*A61M 5/19* (2006.01)
*A61M 5/31* (2006.01)
*A61M 5/315* (2006.01)
*A61M 5/178* (2006.01)

(52) U.S. Cl.
CPC ............ *A61M 5/19* (2013.01); *A61M 5/3134* (2013.01); *A61M 5/31596* (2013.01); *A61M 2005/1787* (2013.01); *A61M 2205/0266* (2013.01)

(58) Field of Classification Search
CPC .. A61M 5/19; A61M 5/3134; A61M 5/31596; A61M 2005/1787; A61M 2205/0266
See application file for complete search history.

(56) References Cited

U.S. PATENT DOCUMENTS

| | | | |
|---|---|---|---|
| 3,164,303 A | 1/1965 | Trautmann | |
| 3,340,873 A | 9/1967 | Solowey | |
| 3,370,754 A | 2/1968 | Cook | |
| 3,739,947 A | 6/1973 | Baumann et al. | |
| 4,055,177 A | 10/1977 | Cohen | |
| 4,613,326 A | 9/1986 | Szwarc | |
| 4,820,286 A | 4/1989 | van der Wal | |
| 5,489,266 A | 2/1996 | Grimard | |
| 5,599,312 A | 2/1997 | Higashikawa | |
| 6,878,338 B2 | 4/2005 | Taylor et al. | |
| 2007/0166660 A1* | 7/2007 | Peuker | A61B 17/00491 433/89 |
| 2008/0114304 A1 | 5/2008 | Nalesso et al. | |
| 2010/0274184 A1* | 10/2010 | Chun | A61M 5/284 604/84 |
| 2012/0101478 A1 | 4/2012 | Stroumpoulis et al. | |
| 2013/0331798 A1 | 12/2013 | Tachikawa et al. | |

OTHER PUBLICATIONS

International Search Report and Written Opinion dated Sep. 14, 2018 in Application No. PCT/US2018/036419.

* cited by examiner

*Primary Examiner* — Imani N Hayman
(74) *Attorney, Agent, or Firm* — Snell & Wilmer L.L.P.

(57) ABSTRACT

A syringe assembly includes a barrel fitted internally with a head of a plunger, an inner plug, an outer plug each slidably engaged to the barrel, and a collapsible framework. A first chamber for containing a solvent is between the head and the inner plug, a second chamber for containing a solute is between the inner plug and the outer plug, and a third chamber containing the collapsible framework is between the outer plug and a discharge end of the barrel. The head, the inner plug, and the outer plug move sequentially through the first, second, and third chambers, respectively, collapsing the framework between the outer plug and the discharge end for sequentially initially mixing the solvent with the solute in the second chamber, turbulent mixing the solvent and the solute in the third chamber, and injecting the solution through the discharge end from the third chamber.

42 Claims, 8 Drawing Sheets

SYRINGE ASSEMBLY

FIELD OF THE INVENTION

The present invention relates generally to drug reconstitution and, more particularly, to a syringe assembly including a barrel fitted internally with a plunger and which contains a solvent and a solute which are mixed into a solution for reconstituting the solute when the plunger is plunged along the barrel.

BACKGROUND OF THE INVENTION

Reconstitution is a process of mixing and diluting solutions. Some medications/drugs supplied in powder form must be mixed with liquid before administration. Many powdered drugs must be stored in powdered form because they rapidly lose their power once they are mixed into a solution. Before powdered drugs can be administered, they must be reconstituted, or mixed with one or more liquids.

In basic terms, reconstitution involves a solute, a solvent, and a solution. The solute, the substance to be dissolved or diluted, i.e. the drug, can be either a solid or a liquid. The solvent, the substance that dissolves/dilutes the solute, is a liquid commonly referred to as the diluent. The resulting mixture is the solution.

Reconstituting of drugs during administration is challenging, requires specialized training, and requires several pieces of equipment and multiple numerous steps that are difficult to carry out and cumbersome, especially in emergency situations. Accordingly, there is a need in the art for a syringe assembly useful for reconstituting and injecting drugs that is simple to use without specialized training, inexpensive, and that does not require oversight by a medical or emergency professional.

SUMMARY OF THE INVENTION

According to the principle of the invention, a syringe assembly includes a barrel arranged about a longitudinal axis and that is fitted internally with a head of a plunger, an inner plug, an outer plug, and a framework. The head, the inner plug, the outer plug, and the framework are each arranged about the longitudinal axis of the barrel. The head, the inner plug, and the outer plug are engaged slidably to the barrel, a first chamber in the barrel for containing a first component is between the head of the plunger and the inner plug, a second chamber in the barrel for containing a second component is between the inner plug and the outer plug, a third chamber in the barrel is between the outer plug and a discharge end of the barrel, and the framework is collapsible and is in the third chamber. The head slides along the barrel and moves through the first chamber to against the inner plug for driving the first component from the first chamber between the barrel and the inner plug and into the second chamber for initially mixing the first component with the second component in the second chamber, when the plunger is plunged along the barrel toward the inner plug from an initial position of the head to a first position of the head. The head and the inner plug concurrently slide along the barrel and the inner plug moves through the second chamber to against the outer plug for driving the first component and the second component from the second chamber between the barrel and the outer plug and into the third chamber, when the plunger is plunged along the barrel toward the outer plug from the first position of the head to a second position of the head. The head, the inner plug, and the outer plug concurrently slide along the barrel and the outer plug moves through the third chamber collapsing the framework between the outer plug and the discharge end for turbulent mixing the first component and the second component in the third chamber into a solution and for injecting the solution through the discharge end of the barrel from the third chamber, when the plunger is plunged along the barrel toward the discharge end from the second position of the head to a plunged position of the head. The first component is one of a solvent and a solute, and the second component is the other one of the solvent and the solute. The framework includes coiled members, the coiled members are coiled helically in a longitudinal direction about the longitudinal axis of the barrel from an upper washer juxtaposed to the outer plug to a lower washer juxtaposed to the discharge end, wherein the outer plug drives the upper washer through the third chamber toward the lower washer collapsing the coiled members therebetween for turbulent mixing the first component and the second component in the third chamber, when the outer plug moves through the third chamber when the plunger is plunged along the barrel from the second position of the head to the plunged position of the head. The outer plug includes a first surface facing the second chamber, and a second surface facing the third chamber, the upper washer includes a disk-shaped plate having a central hole, an upper annular surface facing the second surface of the outer plug, a lower annular surface facing the discharge end, and a perimeter edge, the upper annular surface and the lower annular surface extend outwardly from the central hole to the perimeter edge juxtaposed to the barrel, and the lower washer includes a disk-shaped plate having a central hole, an upper annular surface facing the outer plug, a lower annular surface facing the discharge end, and a perimeter edge, the upper annular surface of the lower washer and the lower annular surface of the lower washer extend outwardly from the central hole of the lower washer to the perimeter edge of the lower washer juxtaposed to the barrel. The central hole of the upper washer enables the first component and the second component to pass therethrough in the third chamber to the coiled members, and the central hole of the lower washer enables the solution to pass therethrough from the coiled members to the discharge end of the barrel. The central hole of the upper washer and the central hole of the lower washer are coaxial with respect to the longitudinal axis of the barrel. The upper annular surface of the upper washer, the lower annular surface of the upper washer, the upper annular surface of the lower washer, and the lower annular surface of the lower washer are parallel relative to each other and to the second surface of the outer plug. The coiled members include an inner coiled member and an outer coiled member. The inner coiled member includes an upper end and a lower end, and is coiled helically about the longitudinal axis of the barrel from the upper end of the inner coiled member connected to the lower annular surface of the upper washer to the lower end of the inner coiled member connected to the upper annular surface of the lower washer, and the outer coiled member includes an upper end and a lower end, and is coiled helically about the longitudinal axis of the barrel and the inner coiled member from the an upper end of the outer coiled member connected to the lower annular surface of the upper washer to the lower end of the outer coiled member connected to the upper annular surface of the lower washer. The outer coiled member includes an inner edge, an outer edge, an upper surface, and a lower surface that together coil helically from the upper end of the outer coiled member connected to the lower annular surface of the upper washer to the lower end of the outer coiled member connected to the upper annular surface of the lower washer, the upper surface of the outer coiled member and the lower surface of the outer coiled member extend outwardly from the inner edge of the outer coiled member to the outer edge of the outer coiled member juxtaposed to the barrel. The inner coiled member includes an inner edge, an outer edge, an upper surface, and a lower surface that together coil helically from the upper end of the inner coiled member connected to the lower annular surface of the upper washer to the lower end of the inner coiled member connected to the upper annular surface of the lower washer, the upper surface of the inner coiled member and the lower surface of the inner coiled member extend outwardly from the inner edge of the inner coiled member to the outer edge of the inner coiled member between the barrel and the outer coiled member. The upper surface of the outer coiled member is flat and the lower surface of the outer coiled member is flat for enabling the upper surface of the outer coiled member and the lower surface of the outer coiled member to turbulent mix the first component and the second component in the third chamber into the solution, when the outer coiled member collapses between the upper washer and the lower washer when the outer plug moves through the third chamber when the plunger is plunged along the barrel from the second position of the head to the plunged position of the head. The upper surface of the inner coiled member is flat and the lower surface of the inner coiled member is flat for enabling the upper surface of the inner coiled member and the lower surface of the inner coiled member to turbulent mix the first component and the second component in the third chamber into the solution, when the inner coiled member collapses between the upper washer and the lower washer when the outer plug moves through the third chamber when the plunger is plunged along the barrel from the second position of the head to the plunged position of the head. The upper surface of the outer coiled member is parallel relative to the lower surface of the outer coiled member, and the upper surface of the inner coiled member is parallel relative to the lower surface of the inner coiled member. The inner coiled member is formed with platforms, the platforms are spaced along the longitudinal axis of the barrel between the central hole of the upper washer and the central hole of the lower washer and cooperate with the inner coiled member and the outer coiled member to turbulent mix the first component and the second component in the third chamber into the solution, when the inner coiled member and the outer coiled member collapse between the upper washer and the lower washer when the outer plug moves through the third chamber when the plunger is plunged along the barrel from the second position of the head to the plunged position of the head. The platforms extend inwardly from the inner edge of the inner coiled member under the central hole of the upper washer and over the central hole of the lower washer, and are parallel relative to each other. The platforms each include an upper surface facing and parallel to the lower annular surface of the upper washer and a lower surface facing and parallel to the upper annular surface of the lower washer. The outer coiled member has shape memory, and the inner coiled member has shape memory. The head of the plunger and the inner plug seal the first chamber from the second chamber, the inner plug and the outer plug seal the second chamber from the first chamber and from the third chamber, all before the plunger is moved from the initial position of the head toward the second position of the head.

According to the principle of the invention, a syringe assembly includes a barrel arranged about a longitudinal axis and that is fitted internally with a plug and a framework each arranged about the longitudinal axis of the barrel. The plug is engaged slidably to the barrel, a chamber in the barrel is between the outer plug and a discharge end of the barrel, and the framework is collapsible and is in the third chamber. The plug slides along the barrel and moves through the chamber collapsing the framework between the outer plug and the discharge end of the barrel for turbulent mixing a first component and a second component in the chamber into a solution, when the plug is plunged along the barrel toward the discharge end from a first position of the plug to a plunged position of the plug toward the discharge end. The first component is one of a solvent and a solute, and the second component is the other one of the solvent and the solute. The framework includes coiled members. The coiled members are coiled helically in a longitudinal direction about the longitudinal axis of the barrel from an upper washer juxtaposed to the outer plug to a lower washer juxtaposed to the discharge end, wherein the outer plug drives the upper washer through the chamber toward the lower washer collapsing the coiled members therebetween, when the outer plug moves through the chamber when the plunger is plunged along the barrel from the second position of the head to the plunged position of the head. The plug includes a surface facing the chamber, the upper washer includes a disk-shaped plate having a central hole, an upper annular surface facing the second surface of the outer plug, a lower annular surface facing the discharge end, and a perimeter edge, the upper annular surface and the lower annular surface extend outwardly from the central hole to the perimeter edge juxtaposed to the barrel, and the lower washer includes a disk-shaped plate having a central hole, an upper annular surface facing the outer plug, a lower annular surface facing the discharge end, and a perimeter edge, the upper annular surface of the lower washer and the lower annular surface of the lower washer extend outwardly from the central hole of the lower washer to the perimeter edge of the lower washer juxtaposed to the barrel. The central hole of the upper washer enables first component and the second component to pass therethrough in the chamber to the coiled members, and the central hole of the lower washer enables the solution to pass therethrough from the coiled members to the discharge end of the barrel. The central hole of the upper washer and the central hole of the lower washer are coaxial with respect to the longitudinal axis of the barrel. The upper annular surface of the upper washer, the lower annular surface of the upper washer, the upper annular surface of the lower washer, and the lower annular surface of the lower washer are parallel relative to each other and to the second surface of the plug. The coiled members include an inner coiled member and an outer coiled member. The inner coiled member includes an upper end and a lower end, and is coiled helically about the longitudinal axis of the barrel from the upper end of the inner coiled member connected to the lower annular surface of the upper washer to the lower end of the inner coiled member connected to the upper annular surface of the lower washer, and the outer coiled member includes an upper end and a lower end, and is coiled helically about the longitudinal axis of the barrel and the inner coiled member from the an upper end of the outer coiled member connected to the lower annular surface of the upper washer to the lower end of the outer coiled member connected to the upper annular surface of the lower washer. The outer coiled member includes an inner edge, an outer edge, an upper surface, and a lower surface that together coil helically from the upper end of the outer coiled member connected to the lower annular surface of the upper washer to the lower end of the outer coiled member connected to the upper annular surface of the lower washer, the upper surface of the outer coiled member and the lower surface of the outer coiled member extend outwardly from the inner edge of the outer coiled member to the outer edge of the outer coiled member juxtaposed to the barrel. The inner coiled member includes an inner edge, an outer edge, an upper surface, and a lower surface that together coil helically from the upper end of the inner coiled member connected to the lower annular surface of the upper washer to the lower end of the inner coiled member connected to the upper annular surface of the lower washer, the upper surface of the inner coiled member and the lower surface of the inner coiled member extend outwardly from the inner edge of the inner coiled member to the outer edge of the inner coiled member between the barrel and the outer coiled member. The upper surface of the outer coiled member is flat and the lower surface of the outer coiled member is flat for enabling the upper surface of the outer coiled member and the lower surface of the outer coiled member to turbulent mix the first component and the second component in the chamber into the solution, when the outer coiled member collapses between the upper washer and the lower washer when the plug is plunged along the barrel toward the discharge end from the first position of the plug to the plunged position of the plug. The upper surface of the inner coiled member is flat and the lower surface of the inner coiled member is flat for enabling the upper surface of the inner coiled member and the lower surface of the inner coiled member to turbulent mix the first component and the second component in the chamber into the solution, when the outer coiled member collapses between the upper washer and the lower washer when the plug is plunged along the barrel toward the discharge end from the first position of the plug to the plunged position of the plug. The upper surface of the outer coiled member is parallel relative to the lower surface of the outer coiled member, and the upper surface of the inner coiled member is parallel relative to the lower surface of the inner coiled member. The inner coiled member is formed with platforms. The platforms are spaced along the longitudinal axis of the barrel between the central hole of the upper washer and the central hole of the lower washer and cooperate with the inner coiled member and the outer coiled member to turbulent mix the first component and the second component in the chamber into the solution, when the inner coiled member and the outer coiled member collapse between the upper washer and the lower washer when the plug is plunged along the barrel toward the discharge end from the first position of the plug to the plunged position of the plug. The platforms extend inwardly from the inner edge of the inner coiled member under the central hole of the upper washer and over the central hole of the lower washer, and are parallel relative to each other. The platforms each include an upper surface facing and parallel to the lower annular surface of the upper washer and a lower surface facing and parallel to the upper annular surface of the lower washer. The outer coiled member has shape memory, and the inner coiled member has shape memory.

According to the principle of the invention, a syringe assembly includes a barrel arranged about a longitudinal axis and that is fitted internally with an inner plug, an outer plug, and a framework each arranged about the longitudinal axis of the barrel. The inner plug and the outer plug are engaged slidably to the barrel, a first chamber in the barrel for containing a first component and a second component initially mixed therein is between the inner plug and the outer plug, a second chamber in the barrel is between the outer plug and a discharge end of the barrel, and the framework is collapsible and is in the second chamber. The inner plug slides along the barrel and moves through the first chamber to against the outer plug for driving the first component and the second component from the first chamber between the barrel and the outer plug and into the second chamber, when the inner plug is plunged along the barrel toward the outer plug from a first position of the inner plug to a second position of the inner plug. The inner plug and the outer plug concurrently slide along the barrel and the outer plug moves through the second chamber collapsing the framework between the outer plug and the discharge end for turbulent mixing the first component and the second component in the second chamber into a solution and for injecting the solution through the discharge end of the barrel from the second chamber, when the inner plug is plunged along the barrel toward the discharge end from the second position of the inner plug to a plunged position of inner plug. The first component is one of a solvent and a solute, and the second component is the other one of the solvent and the solute. The framework includes coiled members. The coiled members are coiled helically in a longitudinal direction about the longitudinal axis of the barrel from an upper washer juxtaposed to the outer plug to a lower washer juxtaposed to the discharge end, wherein the outer plug drives the upper washer through the second chamber toward the lower washer collapsing the coiled members therebetween, when the outer plug moves through the second chamber when the inner plug is plunged along the barrel from the second position of the inner plug to the plunged position of the inner plug. The outer plug includes a first surface facing the first chamber, and a second surface facing the second chamber, the upper washer includes a disk-shaped plate having a central hole, an upper annular surface facing the second surface of the outer plug, a lower annular surface facing the discharge end, and a perimeter edge, the upper annular surface and the lower annular surface extend outwardly from the central hole to the perimeter edge juxtaposed to the barrel, the lower washer includes a disk-shaped plate having a central hole, an upper annular surface facing the outer plug, a lower annular surface facing the discharge end, and a perimeter edge, the upper annular surface of the lower washer and the lower annular surface of the lower washer extend outwardly from the central hole of the lower washer to the perimeter edge of the lower washer juxtaposed to the barrel. The central hole of the upper washer enables the first component and the second component to pass therethrough in the second chamber to the coiled members, and the central hole of the lower washer enables the solution to pass therethrough from the coiled members to the discharge end of the barrel. The central hole of the upper washer and the central hole of the lower washer are coaxial with respect to the longitudinal axis of the barrel. The upper annular surface of the upper washer, the lower annular surface of the upper washer, the upper annular surface of the lower washer, and the lower annular surface of the lower washer are parallel relative to each other and to the second surface of the outer plug. The coiled members include an inner coiled member and an outer coiled member. The inner coiled member includes an upper end and a lower end, and is coiled helically about the longitudinal axis of the barrel from the upper end of the inner coiled member connected to the lower annular surface of the upper washer to the lower end of the inner coiled member connected to the upper annular surface of the lower washer, and the outer coiled member includes an upper end and a lower end, and is coiled helically about the longitudinal axis of the barrel and the inner coiled member from the an upper end of the outer coiled member connected to the lower annular surface of the upper washer to the lower end of the outer coiled member connected to the upper annular surface of the lower washer. The outer coiled member includes an inner edge, an outer edge, an upper surface, and a lower surface that together coil helically from the upper end of the outer coiled member connected to the lower annular surface of the upper washer to the lower end of the outer coiled member connected to the upper annular surface of the lower washer, the upper surface of the outer coiled member and the lower surface of the outer coiled member extend outwardly from the inner edge of the outer coiled member to the outer edge of the outer coiled member juxtaposed to the barrel, and the inner coiled member includes an inner edge, an outer edge, an upper surface, and a lower surface that together coil helically from the upper end of the inner coiled member connected to the lower annular surface of the upper washer to the lower end of the inner coiled member connected to the upper annular surface of the lower washer, the upper surface of the inner coiled member and the lower surface of the inner coiled member extend outwardly from the inner edge of the inner coiled member to the outer edge of the inner coiled member between the barrel and the outer coiled member. The upper surface of the outer coiled member is flat and the lower surface of the outer coiled member is flat for enabling the upper surface of the outer coiled member and the lower surface of the outer coiled member to turbulent mix the first component and the second component in the second chamber into the solution, when the outer coiled member collapses between the upper washer and the lower washer when the outer plug moves through the second chamber when the inner plug is plunged along the barrel from the second position of the inner plug to the plunged position of the inner plug. The upper surface of the inner coiled member is flat and the lower surface of the inner coiled member is flat for enabling the upper surface of the inner coiled member and the lower surface of the inner coiled member to turbulent mix the first component and the second component in the second chamber into the solution, when the inner coiled member collapses between the upper washer and the lower washer when the outer plug moves through the second chamber when the inner plug is plunged along the barrel from the second position of the inner plug to the plunged position of the inner plug. The upper surface of the outer coiled member is parallel relative to the lower surface of the outer coiled member, and the upper surface of the inner coiled member is parallel relative to the lower surface of the inner coiled member. The inner coiled member is formed with platforms. The platforms are spaced along the longitudinal axis of the barrel between the central hole of the upper washer and the central hole of the lower washer and cooperate with the inner coiled member and the outer coiled member to turbulent mix the first component and the second component in the third second into the solution, when the inner coiled member collapses between the upper washer and the lower washer when the outer plug moves through the second chamber when the inner plug is plunged along the barrel from the second position of the inner plug to the plunged position of the inner plug. The platforms extend inwardly from the inner edge of the inner coiled member under the central hole of the upper washer and over the central hole of the lower washer, and are parallel relative to each other. The platforms each include an upper surface facing and parallel to the lower annular surface of the upper washer and a lower surface facing and parallel to the upper annular surface of the lower washer. The outer coiled member has shape memory, and the inner coiled member has shape memory.

BRIEF DESCRIPTION OF THE DRAWINGS

Referring to the drawings.

DETAILED DESCRIPTION

Figure 1:
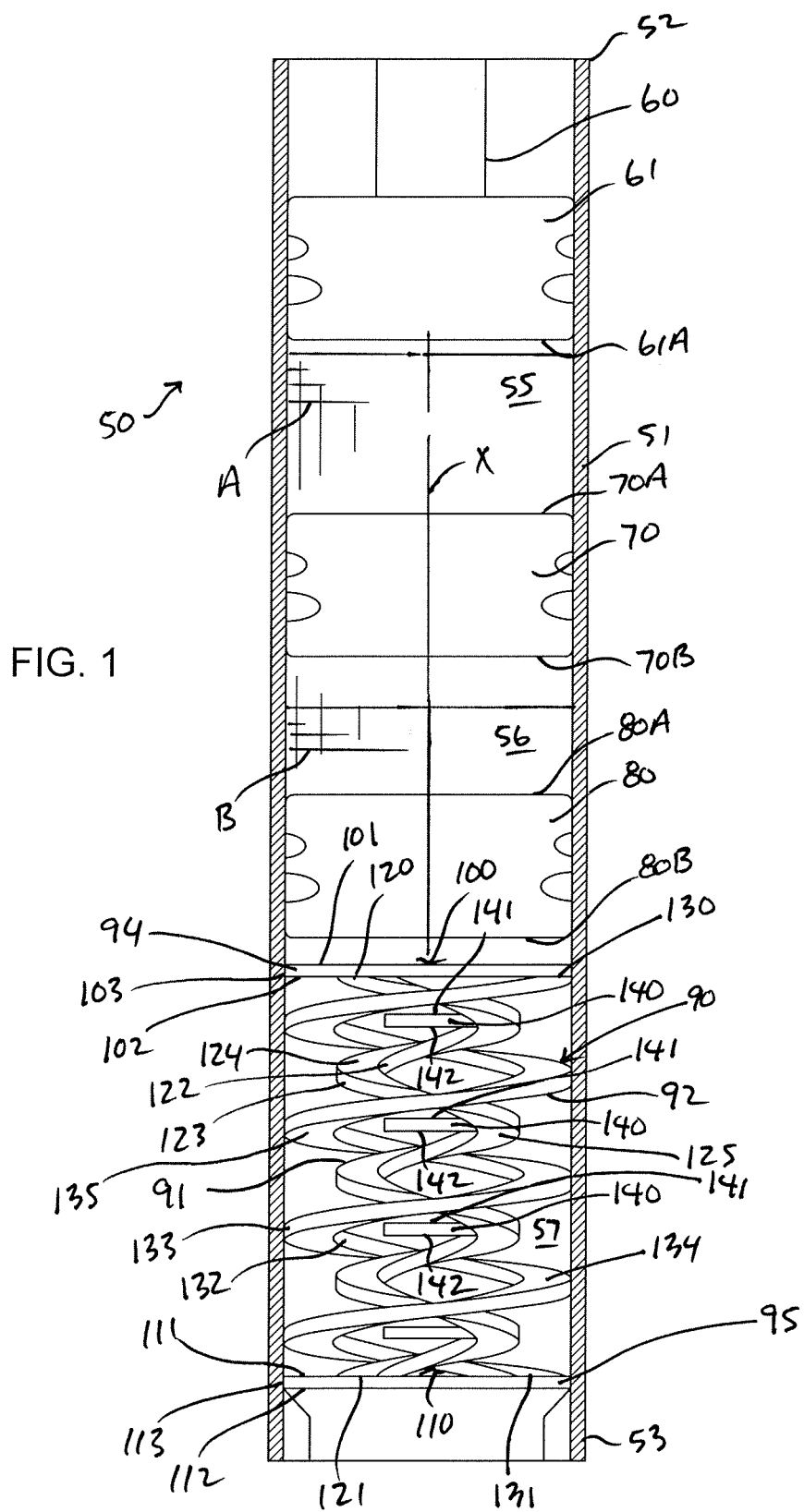
FIG. 1 is a perspective view of a syringe assembly including a barrel having an discharge end, the barrel is sectioned vertically to better illustrate the components therein including a head of a plunger, an inner plug, an outer plug, and a framework, a first chamber in the barrel for containing a first component A between the head of the plunger and the inner plug, a second chamber in the barrel for containing a second component between the inner plug and the outer plug, a third chamber in the barrel between the outer plug and a discharge end of the barrel, and the framework positioned in the third chamber and shown as it would appear in an extended position.

Turning now to the drawings, in which like reference characters indicate corresponding elements throughout the several views, attention is directed to FIG. 1 illustrating a syringe assembly 50. Syringe assembly 50 includes barrel 51, which is sectioned vertically for illustrating the components therein, including head 61 of plunger 60, inner plug 70, outer plug 80, and framework 90. Head 61, inner plug 70, and outer plug 80 are each fashioned of rubber or other like or similar material having the inherent properties of resilience, flexibility, and shape memory. Barrel 51, fashioned, for example, of glass or plastic, has open end 52 that accommodates plunger 60, and an opposed discharge end 53. Discharge end 53 is conventionally arranged for hypodermic needle attachment, nozzle attachment, or tubing attachment. Barrel 51 is arranged about longitudinal axis X. Axis X extends centrally through barrel 51 from open end 52 to discharge end 53. Head 61, inner plug 70, outer plug 80, and framework 90 fitted internally in barrel 51 are each arranged about axis X.

Head 61, inner plug 70, and outer plug 80 are press fit snuggly/closely into barrel 51, are engaged slidably to barrel 51, and are axially spaced-apart so as to form chambers in barrel 51, including chamber 55 in barrel 51 for containing a chosen amount of a component A between head 61 of plunger 60 and inner plug 70, chamber 56 in barrel 51 for containing a chosen amount of a component B between inner plug 70 and outer plug 80, and chamber 57 in barrel 51 between outer plug 80 and discharge end 53 of barrel 51. Framework 90 is collapsible and is chamber 57. Component A is a solvent, namely, a liquid, such as saline or other chosen liquid. Component B is a solute, namely, a liquid solute or a powder solute, and is a chosen medicinal composition. Framework 90 is collapsible from an extended position in FIGS. 1 and 4-6 to a collapsed position in FIG. 8. Chamber 55 is defined between plunging surface 61A of head 61 and upper surface 70A of inner plug 70, chamber 56 is defined between lower surface 70B of inner plug 70 and upper surface 80A of outer plug 80, and chamber 57 is defined between lower surface 80B of outer plug 80 and discharge end 53 of barrel 51. Plunging surface 61A, upper surface 70A, lower surface 70B, upper surface 80A, and lower surface 80B are parallel relative to each other.

In use, framework 90 is fit upright in its extended position into barrel 51 proximate to discharge end 53, outer plug 80 is press fit snuggly/closely into barrel 51 so as to form chamber 57 containing framework 90 between outer plug 80 and discharge end 53. A component B, whether a powder or a liquid, is applied into barrel 51 atop outer plug 80, and inner plug 70 is press fit snuggly/closely into barrel 51 so as to form chamber 56 containing component B. A component A is applied into barrel 51 atop inner plug 70, and head 61 is press fit snuggly/closely into barrel 51 so as to form chamber 55 containing component A. Syringe assembly 50 can be assembled and charged with component A and component B as described and used immediately or pre-packaged for future use.

Figure 4:
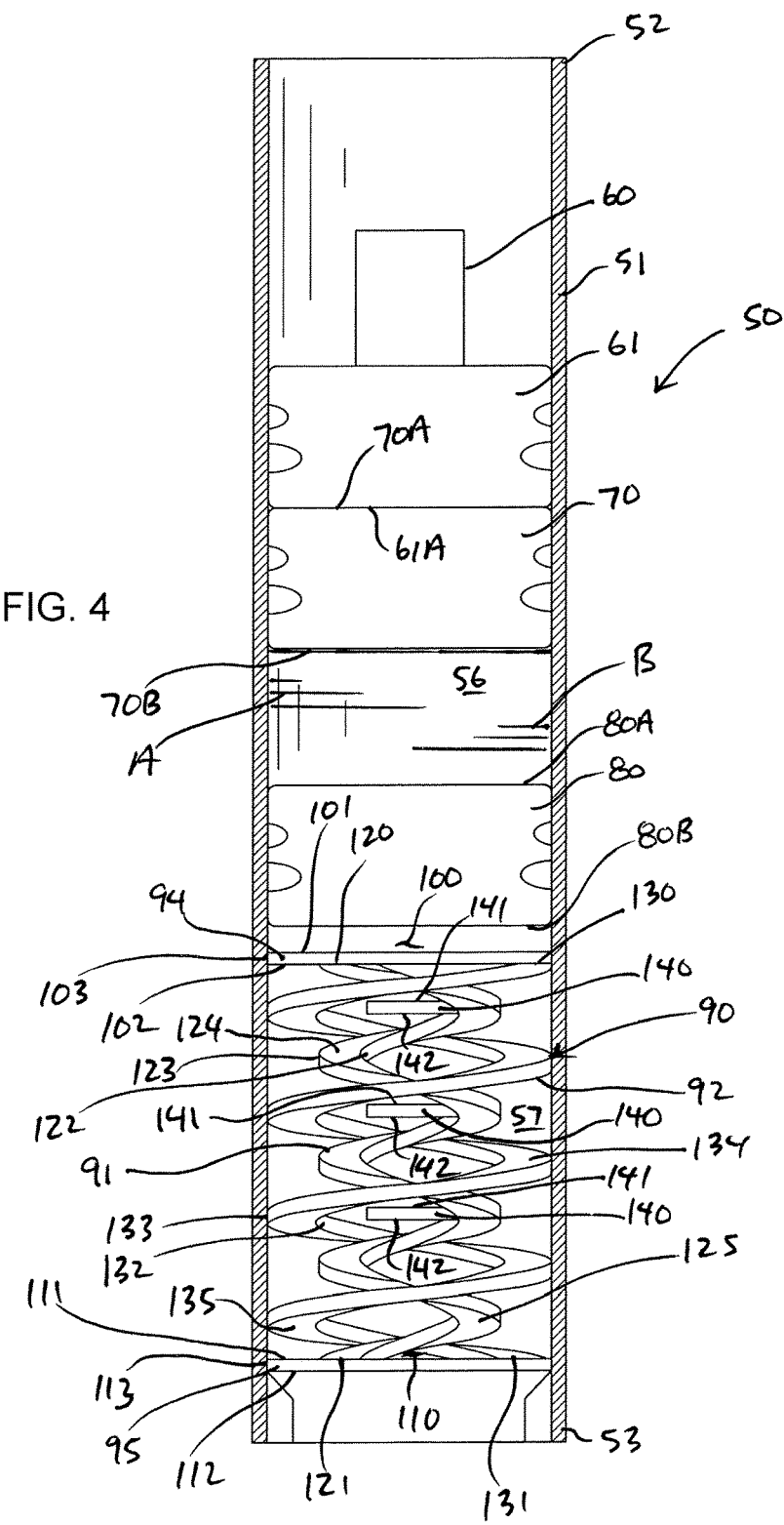
FIG. 4 is a view corresponding to FIG. 1 illustrating the head as it would appear moved along the barrel through the first chamber to against the inner plug for driving the first component from the first chamber between the barrel and the inner plug and into the second chamber for initially mixing the first component with the second component in the second chamber, when the plunger is plunged along the barrel toward the inner plug from an initial position of the head in FIG. 1 to a first position of the head in FIG. 4.

Head 61 slides along barrel 51 and moves through chamber 55 to against inner plug 70 in FIG. 4 for driving component A, via pressure applied against component A by plunging surface 61A, from chamber 55 between barrel 51 and inner plug 70 and into chamber 56 for initially mixing component A with component B in chamber 56, when plunger 60 is pushed/plunged along barrel 51 toward inner plug 70 from an initial position of head 61 in FIG. 1 to a first position of head 61 in FIG. 4 when plunging surface 61A of head 61 comes into direct contact against upper surface 70A of inner plug 70. Chamber 56 is sufficiently sized to accommodate component A and component B therein in FIG. 4. The described configuration of syringe assembly 50 when head 61 is in its first position and when component A and component A are in chamber 56 between inner plug 70 and outer plug 80 constitutes an exemplary embodiment of the invention.

Figure 5:
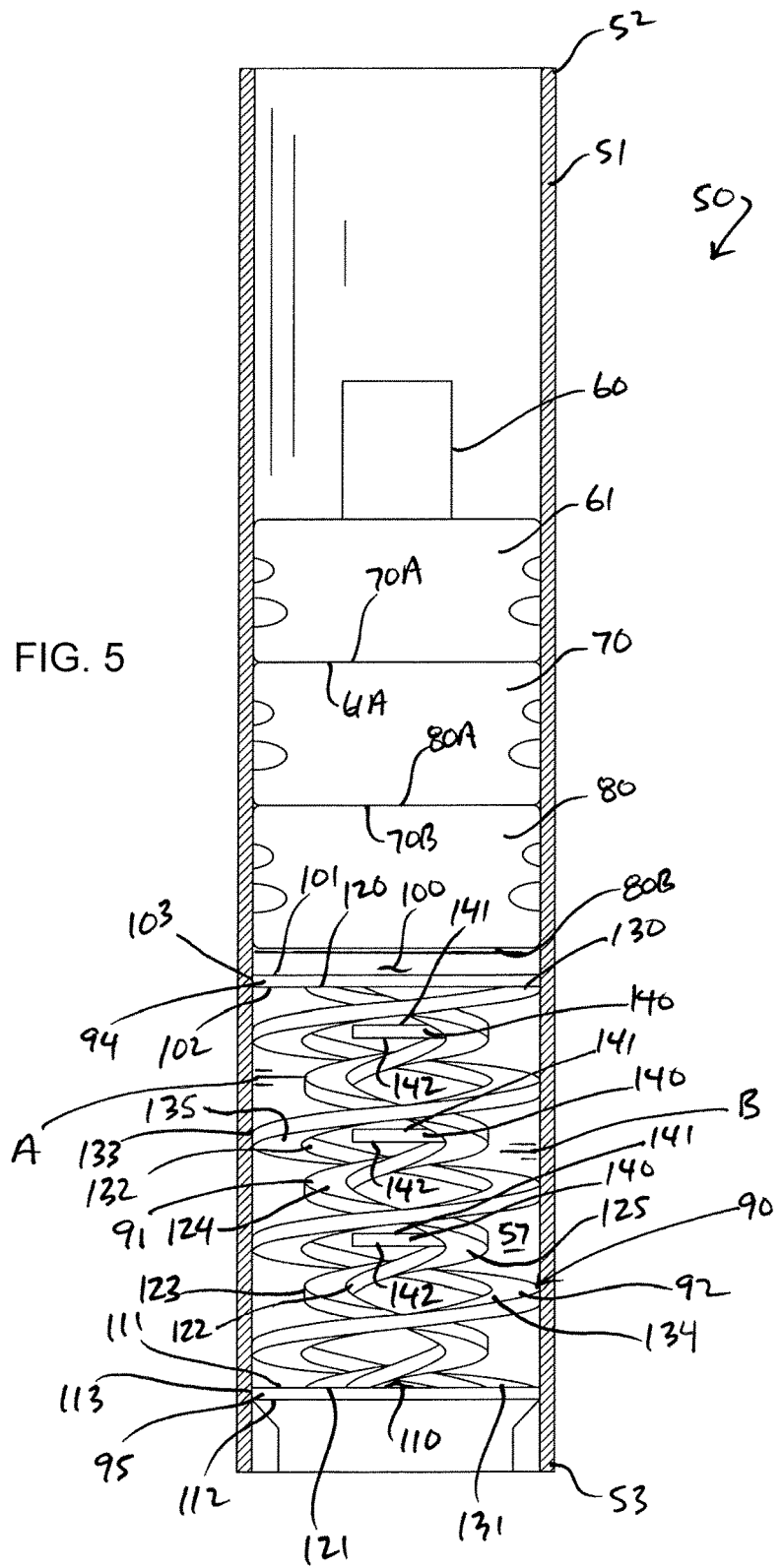
FIG. 5 is a view corresponding to FIG. 4 illustrating the head and the inner plug as they would appear concurrently moved along the barrel and the inner plug moved through the second chamber to against the outer plug for driving the first component and the second component from the second chamber between the barrel and the outer plug and into the third chamber, when the plunger is plunged along the barrel toward the outer plug from the first position of the head in FIG. 4 to a second position of the head in FIG. 5.
Figure 8:
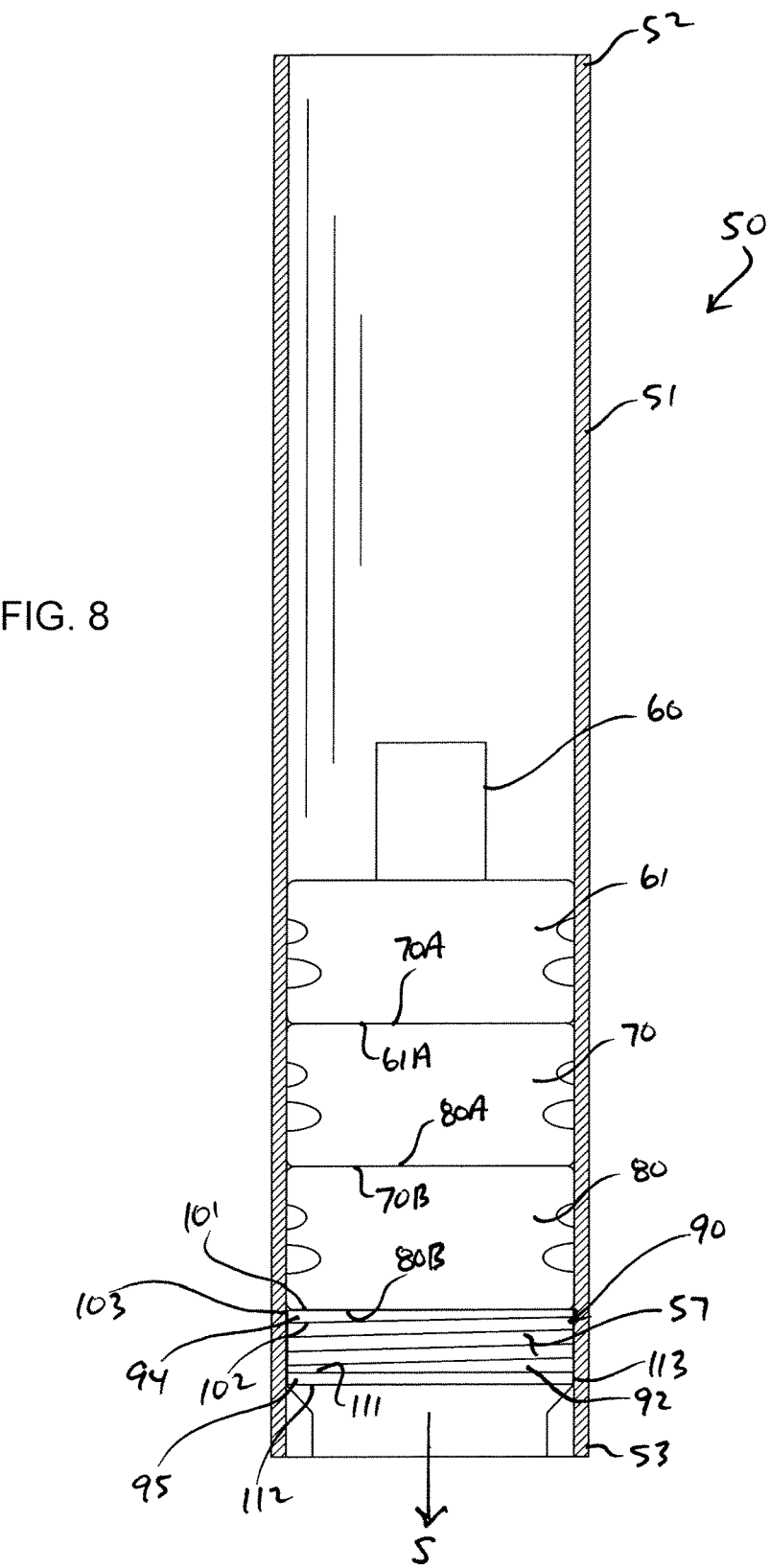
FIG. 8 is a view corresponding to FIG. 7 illustrating the head, the inner plug, and the outer plug concurrently moved along the barrel and the outer plug moved through the third chamber collapsing the framework between the outer plug and the discharge end for turbulent mixing the first component and the second component in the third chamber into the solution and for injecting the solution through the discharge end of the barrel from the third chamber, when the plunger is plunged along the barrel toward the discharge end from the partially plunged position of the head in FIG. 7 to a plunged position of the head in FIG. 8.

Plunging surface 61A of head 61 pushes against upper surface 70A of inner plug 70 and both head 61 and inner plug 70 concurrently slide along barrel 51 and inner plug 70 moves through chamber 56 to against outer plug 80 in FIG. 8 for driving component A and component B, via pressure applied against component A and component B by lower surface 70B of inner plug 70, from chamber 67 between barrel 51 and outer plug 80 and into chamber 57, when plunger 60 is pushed/plunged against inner plug 70 along barrel 51 toward outer plug 80 from the first position of head 61 in FIG. 4 to a second position of head 61 in FIG. 5 when lower surface 70B of inner plug 70 comes into direct contact against upper surface 80A of outer plug 80. Chamber 57 is sufficiently sized to accommodate component A, component B, and framework 90 therein in FIG. 5. The described configuration of syringe assembly 50 when head 61 is in its second position and when component A and component A are in chamber 57 between outer plug 80 and discharge end 53 constitutes an exemplary embodiment of the invention.

Figure 6:
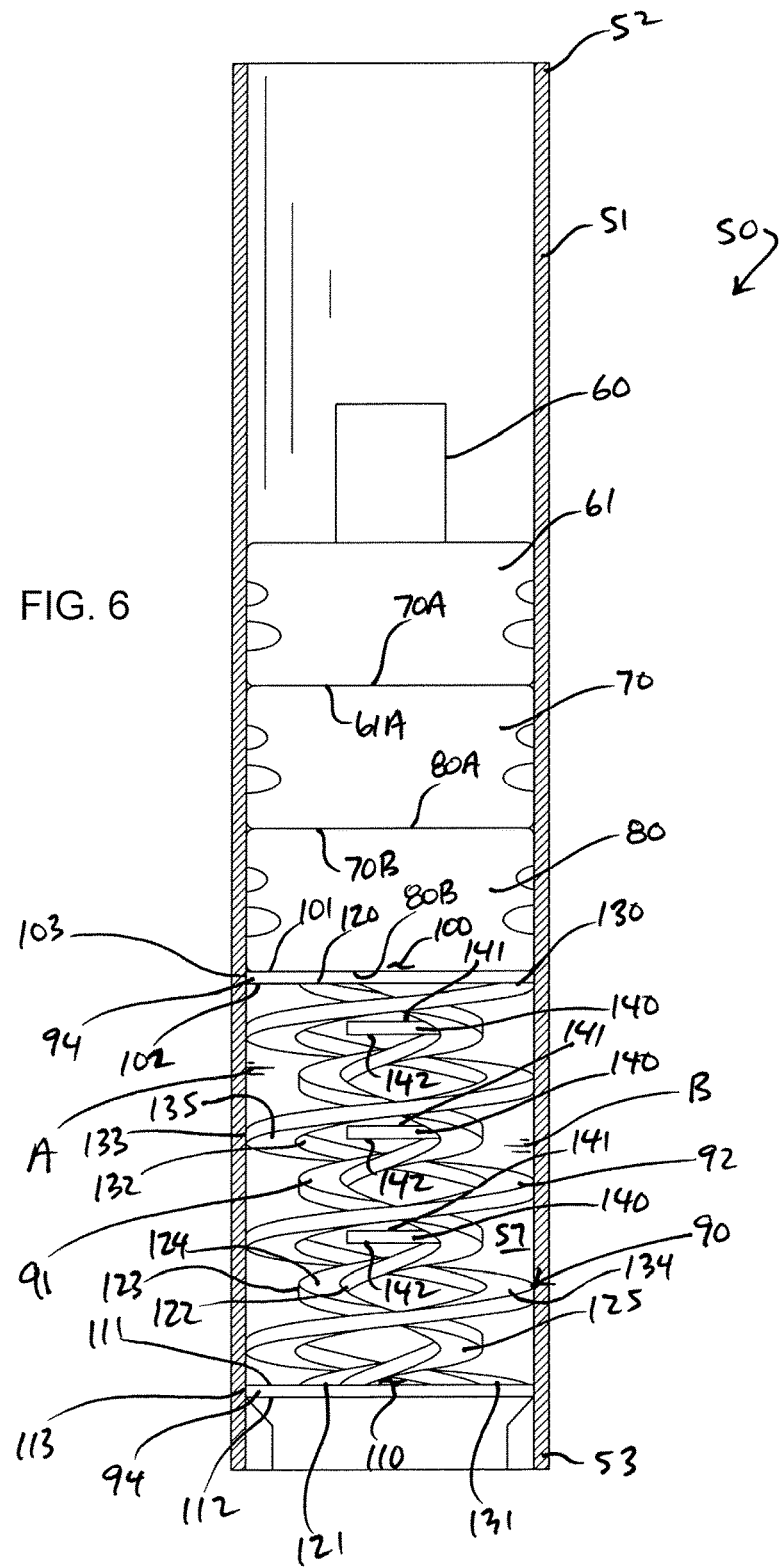
FIG. 6 is a view corresponding to FIG. 5 illustrating the head, the inner plug, and the outer plug concurrently moved along the barrel and the outer plug moved partially through the third chamber to against the framework, when the plunger is plunged along the barrel toward the discharge end to beyond the second position of the head in FIG. 5.
Figure 7:
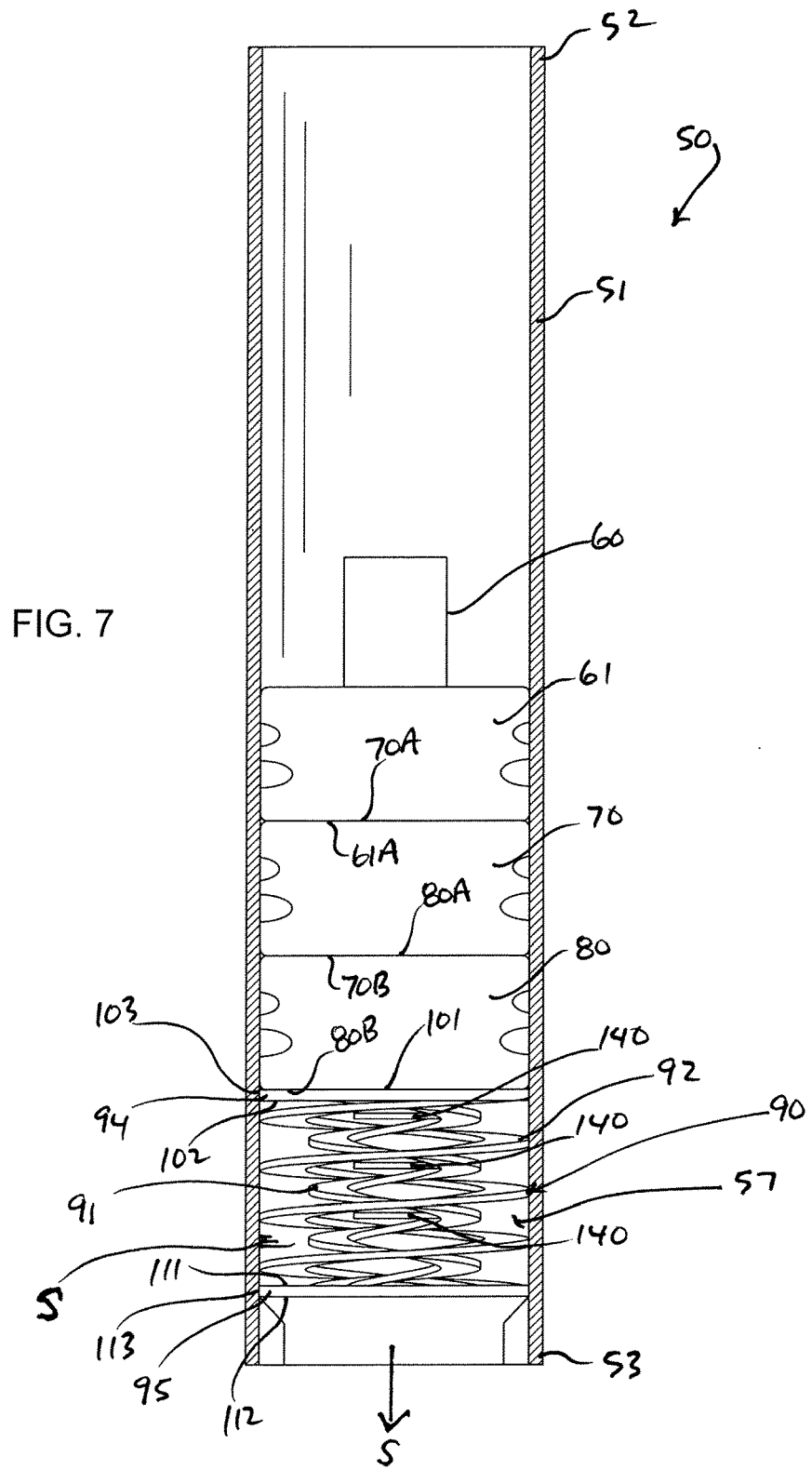
FIG. 7 is a view corresponding to FIG. 6 illustrating the head, the inner plug, and the outer plug concurrently moved along the barrel and the outer plug moved partially through the third chamber partially collapsing the framework between the outer plug and the discharge end for turbulent mixing the first component and the second component in the third chamber into a solution, when the plunger is plunged along the barrel toward the discharge end from the second position of the head in FIG. 5 to beyond the position of the head in FIG. 6 to a partially plunged position of the head in FIG. 7.

Plunging surface 61A of head 61 pushes against upper surface 70A of inner plug 70 and at the same time lower surface 70B of inner plug 70 pushes against upper surface 80A of outer plug and all concurrently slide along barrel 51 and outer plug 80 moves through chamber 57 to against framework 90 in FIGS. 6-8 collapsing framework 90 in FIGS. 7 and 8, via pressure applied against framework 90 by lower surface 80B of outer plug 80, between lower surface 80B of outer plug 80 and discharge end 53 for automatically turbulating or turbulent mixing component A and component B in chamber 57 into a solution S and for injecting solution S through discharge end 53 of barrel 51 from chamber 57, via pressure applied against component A and component B and the resulting solution S by lower surface 80B of outer plug 80, when plunger 60 is pushed/plunged against inner plug 70 and inner plug 70 concurrently pushes/plunged against outer plug 80 along barrel 51 toward discharge end 53 from the second position of head 61 in FIG. 5 to a plunged position of head 61 in FIG. 8. FIGS. 5 and 6 illustrate framework 90 as it would appear at-rest and not collapsed, namely, extended, and FIG. 6 illustrates lower surface 80B of outer plug 80 in initial contact with upper annular surface 101 of washer 94, when head 60 is initially displaced downwardly from it second position in FIG. 5, FIG. 7 illustrates framework 90 as it would appear partially collapsed between lower surface 80B of outer plug 80 and discharge end 53 of barrel 51, when head 61 is in an intermediate position between its second position in FIG. 5 and its plunged position in FIG. 8, and FIG. 8 illustrates framework as it would appear collapsed, namely, fully collapsed, between lower surface 80B of outer plug 80 and discharge end 53 of barrel 51. Outer surface 80B of outer plug 80 pushes against component A and component B in chamber 57, pushes against upper annular surface 101 of upper washer 94 and collapses framework 90 between upper washer 94 and lower washer 95, while at the same time framework 90 acts on component A and component B being forced through chamber 57 via pressure applied against component A and component B in chamber 57 via lower surface 80B of outer plug 80 to automatically "turbulate" or turbulent mix component A and component B into solution S and inject solution S outwardly through discharge end 53, when framework 90 collapses from its extended position in FIG. 5 to its collapsed position in FIG. 8 when outer plug 80 moves along barrel 51 through chamber 57 from the second position of head 61 in FIG. 5 to the plunged position of head 61 in FIG. 8.

Head 61 of plunger 60 and inner plug 70 seal chamber 55 and component A therein from chamber 56, and inner plug 70 and outer plug 80 seal chamber 56 and component B therein from chamber 55 and from chamber 57, all before plunger 60 is moved from the initial position of head 61 in FIG. 1 toward the second position of head in FIG. 5. Inner plug 70, outer plug 80, and framework 90 displace sequentially when plunger is plunged along barrel 51 from the initial position of head 61 in FIG. 5 to the plunged position of head 61 in FIG. 8. Head 61 of plunger 60, inner plug 70, and outer plug 80 translate along longitudinal axis X of barrel 51, and framework 90 collapses along longitudinal axis X of barrel 51.

In FIG. 1, framework 90 includes coiled members 91 and 92, upper washer 94, and lower washer 95. Framework 90 is fashioned of a non-reactive material or combination of materials, such as medical grade plastic or metal, having a shape memory material characteristic. Accordingly, inner coiled member 91 and outer coiled member 92 each have shape memory. Coiled members 91 and 92 are helical coils that coil upright helically in a longitudinal direction about longitudinal axis X of barrel 51 from upper washer 94 juxtaposed to and under lower surface 80B of outer plug 80 to lower washer 95 against, and juxtaposed to, discharge end 53. Framework 90 extends upright in chamber 57 from lower washer 95 seated on discharge end 53 to upper washer 94 toward outer plug 80, and coiled members are coiled upright helically in a longitudinal direction about axis X from lower washer 95 to upper washer 94. Outer plug 80 drives upper washer 94 through chamber 57 toward lower washer 95 collapsing coiled members 91 and 92 therebetween for automatically "turbulating" or turbulent mixing component A and component B in chamber 57, when outer plug 80 moves through chamber 57 when plunger 60 is plunged along the barrel from the second position of head 61 in FIG. 5 to the plunged position of head 61 in FIG. 8.

Figure 2:
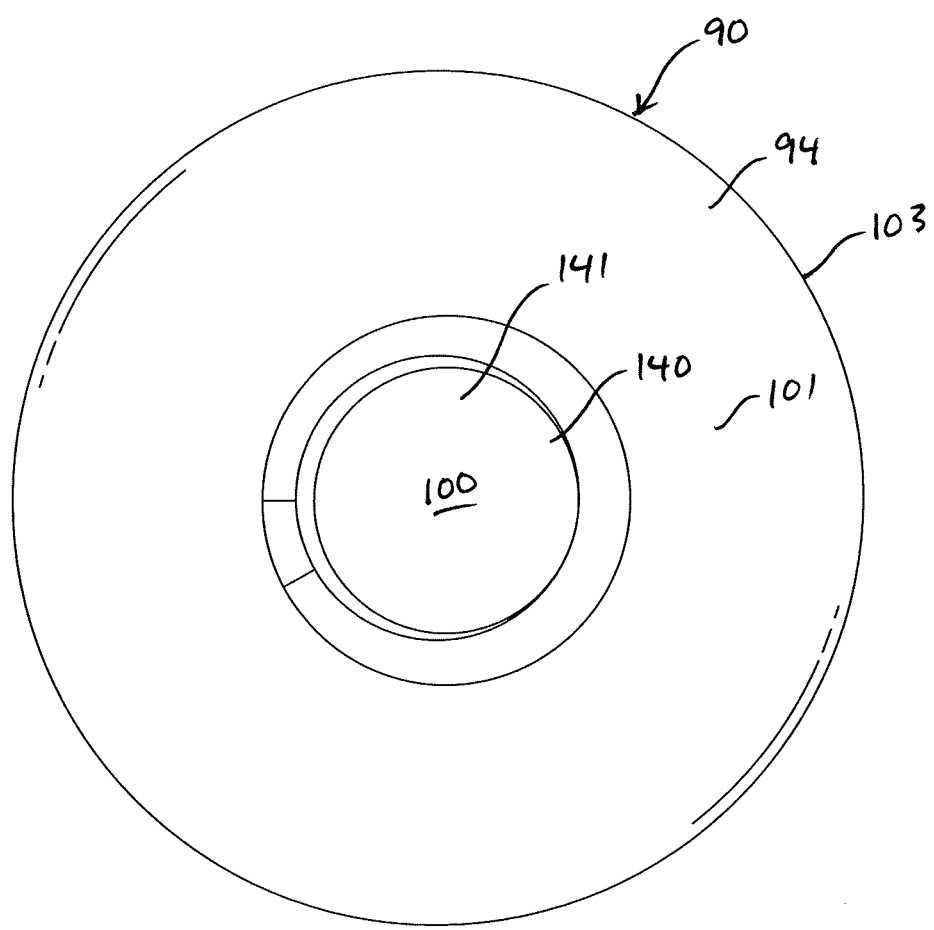
FIG. 2 is a top plan view of the framework of FIG. 1.
Figure 3:
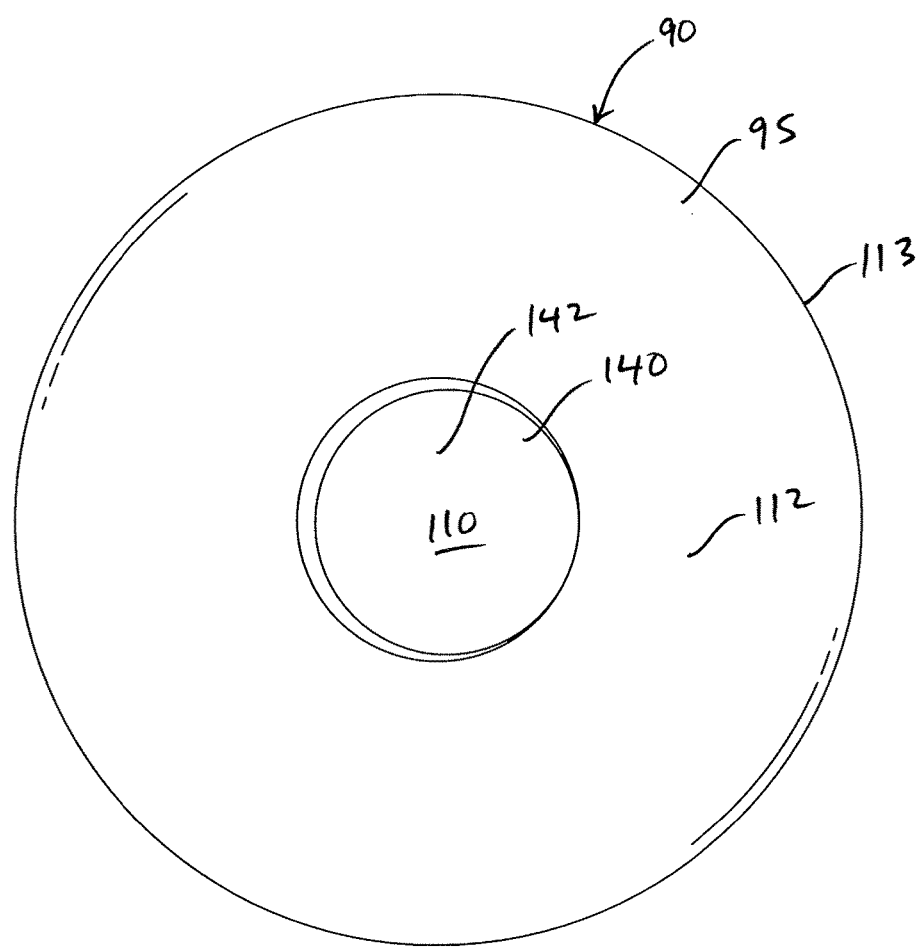
FIG. 3 is a bottom plan view of the embodiment of FIG. 2.

Upper surface 80A of outer plug 80 faces chamber 56, and lower surface 80B of outer plug 80 faces chamber 57. Upper and lower washers 94 and 95 are identical. Upper washer 94 is a disk-shaped plate having central hole 100 in FIG. 2, upper annular surface 101 facing lower surface 80B of outer plug 80, lower annular surface 102 facing discharge end 53, and perimeter edge 103. Upper annular surface 101 and lower annular surface 102 extend outwardly from central hole 100 to perimeter edge 103 juxtaposed to barrel 51. Lower washer 95 is a disk-shaped plate having central hole 110 in FIG. 3, upper annular surface 111 facing lower surface 80B of outer plug 80, lower annular surface 112 facing discharge end 53, and perimeter edge 113. Upper annular surface 111 of lower washer 95 and lower annular surface 112 of lower washer 95 extend outwardly from central hole 110 of lower washer 95 to perimeter edge 113 juxtaposed to barrel 51.

Central hole 100 of upper washer 94 enables component A and component B to pass therethrough in chamber 57 to coiled members 91 and 92, when outer plug 80 moves through chamber 57 from the second position of head 61 in FIG. 5 to when lower surface 80B of outer plug 80 comes into direct contact against upper annular surface 101 of upper washer 94. Central hole 110 of lower washer 95 enables solution S, the mixture of component A and component B, to pass therethrough from coiled members 91 and 92 to discharge end 53 of barrel 51. Central hole 100 of upper washer 94 and central hole 110 of lower washer 95 are coaxial with respect to axis X of barrel 51. Upper annular surface 101, lower annular surface 102, upper annular surface 111, and lower annular surface 112 are parallel relative to each other and to plunging surface 61A, upper surface 70A, lower surface 70B, upper surface 80A, and lower surface 80B.

Coiled members 91 and 92 include inner coiled member 91 and outer coiled member 92. Inner coiled member 91, a helical coil, includes upper end 120 and lower end 121, and is coiled about longitudinal axis X of barrel 51 from upper end 120 connected to lower annular surface 102 of upper washer 94 to lower end 121 connected to upper annular surface 111 of lower washer 95. Outer coiled member 92, a helical coil, includes upper end 130 and lower end 131, and is coiled about axis X of barrel 51 and inner coiled member 91 from upper end 130 connected to lower annular surface 102 of upper washer 94 to lower end 131 connected to upper annular surface 111 of lower washer 95. Upper washer 94 moves toward lower washer 95 and perimeter edge 103 thereof slides along barrel and inner and outer coiled members 91 and 92 collapse, outer coiled member 92 about inner coiled member 91, and outer edge 133 of outer coiled member 92 slides along barrel, between upper and lower washers 94 and 95, when framework 90 collapses from its extended position in FIG. 5 to its collapsed position in FIG. 8. Perimeter edge 103 of upper washer 94, perimeter edge 113 of lower washer 95, and outer edge 123 of outer coiled member 92

Outer coiled member 92 includes inner edge 132, outer edge 133, upper surface 134, and lower surface 135 that together coil helically from upper end 130 of outer coiled member 92 to lower end 131 of outer coiled member 92. Upper surface 134 of outer coiled member 92 and lower surface 135 of outer coiled member 92 are deflecting surfaces that extend outwardly from inner edge 132 to outer edge 133 juxtaposed to the barrel.

Inner coiled member 91 includes inner edge 122, outer edge 123, upper surface 124, and lower surface 125 that together coil helically from upper end 120 of inner coiled member 91 to the lower end 121 of inner coiled member 91. Upper surface 124 of inner coiled member 91 and lower surface 125 of inner coiled member 91 are deflecting surfaces that extend outwardly from inner edge 122 of inner coiled member 91 to outer edge 123 of inner coiled member 91 between barrel 51 and inner edge 132 of outer coiled member 92.

Upper surface 134 of outer coiled member 92 is flat and lower surface 135 of outer coiled member 92 is flat for enabling upper surface 134 and lower surface 134 of outer coiled member 92 to act deflectively on component A and component B in chamber 57 to turbulate or turbulent mix component A and component B in chamber 57 into solution S, when outer coiled member 92 collapses between upper washer 94 and lower washer 95, when outer plug 80 moves through chamber 57 and pushes against component A and component B in chamber 57 when plunger 60 is plunged along barrel 51 from the second position of head 61 in FIG. 5 to the plunged position of head 61 in FIG. 8. Upper surface 124 of inner coiled member 91 is flat and lower surface 125 of inner coiled member 91 is flat for enabling upper surface 124 and lower surface 125 of inner coiled member 91, at the same time as outer coiled member 92, to act deflectively on component A and component B in chamber 57 to turbulate or turbulent mix component A and component B in chamber 57 into solution S, when inner coiled member 91 collapses between upper washer 94 and lower washer 95, when outer plug 80 moves through chamber 57 and pushes against component A and component B in chamber 57 when plunger 60 is plunged along barrel 51 from the second position of head 61 in FIG. 5 to the plunged position of head 61 in FIG. 8. In this example, upper surface 134 and lower surface 135 of outer coiled member 92 are parallel relative to each other, and upper surface 124 and lower surface 125 of inner coiled member 91 are parallel relative to each other.

In FIG. 1, inner coiled member 91 is formed platforms 140. Platforms 140 are spaced along axis X of barrel 51 between central hole 100 of upper washer 94 and central hole 110 of lower washer 95 and cooperate concurrently with inner coiled member 91 and outer coiled member 95 to squeeze therebetween to turbulent mix component A and component B in chamber 57 into solution S, when inner coiled member 91 and outer coiled member 92 collapse between upper washer 94 and lower washer 95 when outer plug 80 moves through chamber 57 and pushes against component A and component B in chamber when plunger 60 is plunged along barrel 51 from the second position of head 61 in FIG. 5 to the plunged position of head 61 in FIG. 8. Platforms 140 extend inwardly from inner edge 122 of inner coiled member 91 under central hole 100 of upper washer 94 and over central hole 110 of lower washer 95, and are parallel relative to other and to upper and lower washers 94 and 94, and to head 61, inner plug 70, and outer plug 80. Platforms 140 each include deflecting surfaces, including upper surface 141 facing and parallel to lower annular surface 102 of upper washer 94 and lower surface 142 facing and parallel to upper annular surface 111 of lower washer 95. Upper and lower washers 94 and 95 move toward one another, inner and outer coiled members 91 collapse, outer coiled member 92 about inner coiled member 91, between upper and lower washers 94 and 95, and platforms 140 move together, one atop the other within inner coiled member 91, when framework 90 collapses from its extended position in FIG. 5 to its collapsed position in FIG. 8. The described deflecting surfaces of inner coiled member 91, outer coiled member 92, and platforms 140 cooperate to automatically turbulate or turbulent mix component A and component B in chamber 57, squeezing and deflecting components A and B therebetween the deflecting surfaces, when framework 90 collapses from its extended position in FIG. 5 to its collapsed position in FIG. 8 when at the same time plug 80 moves through chamber 57 from the second position of head 61 in FIG. 5 to the plunged position of head 61 in FIG. 8 forcing component A and component B through framework 90 and the resulting solution through central hole 110 of lower washer 95 to discharge end 53. Lower surface 80B of outer plug 80 comes into direct contact against upper annular surface 101 of upper washer 94 and drives upper washer 94 through chamber 57 toward lower washer 95 collapsing coiled members 91 and 92 therebetween for turbulent mixing component A and component B in chamber 57, when outer plug 80 moves through chamber 57 when plunger 60 is plunged along the barrel from the second position of head 61 in FIG. 5 to the plunged position of head 61 in FIG. 8. Framework 90 assumes an inherently compact shape of a puck in chamber 57 and occupies the dead space in chamber 57, with collapsed outer coiled member 92 coiled about collapsed inner coiled member 91 coiled about platforms 140 sandwiched one atop the other all between lower annular surface 102 of upper washer 94 and upper annular surface 111 of lower washer 95, when framework 90 is in its collapsed position in FIG. 8. In other words, after solution S is injected from chamber 57 through discharge end 53, framework 90, collapsed into its puck-shaped collapsed position in FIG. 8, is left in, and occupies, the resulting dead space in chamber 57.

With framework 90 fit upright in its extended position in chamber 57 between outer plug 80 and discharge end 53, component B in chamber 56 between inner plug 70 and outer plug 80, and component A in chamber 55 between head 61 and inner plug 70, component A and component B are mixed into solution S in chamber 57, and component B is reconstituted, at the time of injection when head 61 is pushed/plunged through barrel 51 from its initial position in FIG. 1 to its plunged position in FIG. 8, in which component A is driven from chamber 55 to chamber 56 when head 61 moves from its initial position in FIG. 1 to its first position against inner plug 70 in FIG. 4 to initially mix component A with component B in chamber 56, component A and component B are driven by inner plug 70 from chamber 56 to chamber 57 when head 61 is plunged through barrel 51 from its first position in FIG. 4 to its second position in FIG. 5, and component B and component B are driven by outer plug 80 from chamber 57 through discharge end 53 when head 61 is plunged through barrel 51 from its second position in FIG. 5 to its plunged position in FIG. 8. At the same time outer plug 80 moves through chamber from the second position of head 61 in FIG. 5 to the plunged position of head 61 in FIG. 8, framework 90 collapses and acts on component A and component B in chamber 57 while it is collapsing to turbulate or turbulent mix component A and component B into solution S in chamber 57 before solution S ejects outwardly through discharge end 53 from chamber 57. After a single use, plunger 60, inner plug 70, outer plug, and framework 90 can be withdrawn from barrel 51 and, after cleaning, such as by autoclaving, reused. Because framework 90 is has shape memory, it will assume its extended position when outer plug 80 and framework 90 are withdrawn from barrel 51.

Volume 55 is charged with a chosen amount of component A and volume 56 is charged with a chosen amount of component B so as to result in solution S having a chosen concentration of component B. In the present embodiment, volume 57 is charged with framework 90. If desired, volume 57 may be additionally charged with a chosen amount of a solvent to be mixed with component A and component B to form solution S in the use of syringe assembly 50. Ultimately, the concentration of component B in solution S is determined by the relative amounts of component A and component B. The combination of the chosen amount of component A, the chosen amount of component B, and the chosen amount of the solvent in chamber 57 accompanied by framework 90 would be arranged to result in the resulting solution S having a chosen concentration of component B.

In the present embodiment, volume 55 is charged with a chosen amount of component A, a chosen solvent, and volume 56 is charged with a chosen amount of component B, a chosen solute, so as to result in solution S having a chosen concentration of component B. In an alternate embodiment, component A in chamber 55 is a chosen solute, a chosen liquid solute, and component B in chamber 56 is a chosen solvent, a chosen liquid solvent. The use and implementation of syringe assembly 50 is as described above when chamber 55 is charged with a chosen liquid solute and chamber 56 is charged with a chosen liquid solvent.

The present invention is described above with reference to illustrative embodiments. However, those skilled in the art will recognize that changes and modifications may be made in the described embodiments without departing from the nature and scope of the present invention. Various further changes and modifications to the embodiments herein chosen for purposes of illustration will readily occur to those skilled in the art. To the extent that such modifications and variations do not depart from the spirit of the invention, they are intended to be included within the scope thereof.

What is claimed is:

1. A syringe assembly, comprising:
a barrel, the barrel is arranged about a longitudinal axis and is fitted internally with a head of a plunger, an inner plug, an outer plug, and a framework, the head, the inner plug, the outer plug, and the framework are each arranged about the longitudinal axis of the barrel, the head, the inner plug, and the outer plug are engaged slidably to the barrel, a first chamber in the barrel for containing a first component is between the head of the plunger and the inner plug, a second chamber in the barrel for containing a second component is between the inner plug and the outer plug, a third chamber in the barrel is between the outer plug and a discharge end of the barrel, and the framework is collapsible and is in the third chamber;
the head slides along the barrel and moves through the first chamber to against the inner plug for driving the first component from the first chamber between the barrel and the inner plug and into the second chamber for initially mixing the first component with the second component in the second chamber, when the plunger is plunged along the barrel toward the inner plug from an initial position of the head to a first position of the head;
the head and the inner plug concurrently slide along the barrel and the inner plug moves through the second chamber to against the outer plug for driving the first component and the second component from the second chamber between the barrel and the outer plug and into the third chamber, when the plunger is plunged along the barrel toward the outer plug from the first position of the head to a second position of the head; and
the head, the inner plug, and the outer plug concurrently slide along the barrel and the outer plug moves through the third chamber collapsing the framework between the outer plug and the discharge end for turbulent mixing the first component and the second component in the third chamber into a solution and for injecting the solution through the discharge end of the barrel from the third chamber, when the plunger is plunged along the barrel toward the discharge end from the second position of the head to a plunged position of the head;
wherein the first component is one of a solvent and a solute, and the second component is the other one of the solvent and the solute.

2. The syringe assembly according to claim 1, wherein the framework comprises coiled members, the coiled members are coiled helically in a longitudinal direction about the longitudinal axis of the barrel from an upper washer juxtaposed to the outer plug to a lower washer juxtaposed to the discharge end, wherein the outer plug drives the upper washer through the third chamber toward the lower washer collapsing the coiled members therebetween for turbulent mixing the first component and the second component in the third chamber, when the outer plug moves through the third chamber when the plunger is plunged along the barrel from the second position of the head to the plunged position of the head.

3. The syringe assembly according to claim 2, wherein:
the outer plug includes a first surface facing the second chamber, and a second surface facing the third chamber;
the upper washer comprises a disk-shaped plate having a central hole, an upper annular surface facing the second surface of the outer plug, a lower annular surface facing the discharge end, and a perimeter edge, the upper annular surface and the lower annular surface extend outwardly from the central hole to the perimeter edge juxtaposed to the barrel; and
the lower washer comprises a disk-shaped plate having a central hole, an upper annular surface facing the outer plug, a lower annular surface facing the discharge end, and a perimeter edge, the upper annular surface of the lower washer and the lower annular surface of the lower washer extend outwardly from the central hole of the lower washer to the perimeter edge of the lower washer juxtaposed to the barrel;
wherein the central hole of the upper washer enables the first component and the second component to pass therethrough in the third chamber to the coiled members, and the central hole of the lower washer enables the solution to pass therethrough from the coiled members to the discharge end of the barrel.

4. The syringe assembly according to claim 3, wherein the central hole of the upper washer and the central hole of the lower washer are coaxial with respect to the longitudinal axis of the barrel.

5. The syringe assembly according to claim 4, wherein the upper annular surface of the upper washer, the lower annular surface of the upper washer, the upper annular surface of the lower washer, and the lower annular surface of the lower washer are parallel relative to each other and to the second surface of the outer plug.

6. The syringe assembly according to claim 5, wherein the coiled members comprise:
an inner coiled member and an outer coiled member;
the inner coiled member includes an upper end and a lower end, and is coiled helically about the longitudinal axis of the barrel from the upper end of the inner coiled member connected to the lower annular surface of the upper washer to the lower end of the inner coiled member connected to the upper annular surface of the lower washer; and
the outer coiled member includes an upper end and a lower end, and is coiled helically about the longitudinal axis of the barrel and the inner coiled member from the an upper end of the outer coiled member connected to the lower annular surface of the upper washer to the lower end of the outer coiled member connected to the upper annular surface of the lower washer.

7. The syringe assembly according to claim 6, wherein:
the outer coiled member includes an inner edge, an outer edge, an upper surface, and a lower surface that together coil helically from the upper end of the outer coiled member connected to the lower annular surface of the upper washer to the lower end of the outer coiled member connected to the upper annular surface of the lower washer, the upper surface of the outer coiled member and the lower surface of the outer coiled member extend outwardly from the inner edge of the outer coiled member to the outer edge of the outer coiled member juxtaposed to the barrel; and the inner coiled member includes an inner edge, an outer edge, an upper surface, and a lower surface that together coil helically from the upper end of the inner coiled member connected to the lower annular surface of the upper washer to the lower end of the inner coiled member connected to the upper annular surface of the lower washer, the upper surface of the inner coiled member and the lower surface of the inner coiled member extend outwardly from the inner edge of the inner coiled member to the outer edge of the inner coiled member between the barrel and the outer coiled member.

8. The syringe assembly according to claim 7, wherein the upper surface of the outer coiled member is flat and the lower surface of the outer coiled member is flat for enabling the upper surface of the outer coiled member and the lower surface of the outer coiled member to turbulent mix the first component and the second component in the third chamber into the solution, when the outer coiled member collapses between the upper washer and the lower washer when the outer plug moves through the third chamber when the plunger is plunged along the barrel from the second position of the head to the plunged position of the head.

9. The syringe assembly according to claim 8, wherein the upper surface of the inner coiled member is flat and the lower surface of the inner coiled member is flat for enabling the upper surface of the inner coiled member and the lower surface of the inner coiled member to turbulent mix the first component and the second component in the third chamber into the solution, when the inner coiled member collapses between the upper washer and the lower washer when the outer plug moves through the third chamber when the plunger is plunged along the barrel from the second position of the head to the plunged position of the head.

10. The syringe assembly according to claim 9, wherein:
the upper surface of the outer coiled member is parallel relative to the lower surface of the outer coiled member; and
the upper surface of the inner coiled member is parallel relative to the lower surface of the inner coiled member.

11. The syringe assembly according to claim 10, wherein the inner coiled member is formed with platforms, the platforms are spaced along the longitudinal axis of the barrel between the central hole of the upper washer and the central hole of the lower washer and cooperate with the inner coiled member and the outer coiled member to turbulent mix the first component and the second component in the third chamber into the solution, when the inner coiled member and the outer coiled member collapse between the upper washer and the lower washer when the outer plug moves through the third chamber when the plunger is plunged along the barrel from the second position of the head to the plunged position of the head.

12. The syringe assembly according to claim 11, wherein the platforms extend inwardly from the inner edge of the inner coiled member under the central hole of the upper washer and over the central hole of the lower washer, and are parallel relative to each other.

13. The syringe assembly according to claim 12, wherein the platforms each include an upper surface facing and parallel to the lower annular surface of the upper washer and a lower surface facing and parallel to the upper annular surface of the lower washer.

14. The syringe assembly according to claim 13, wherein the outer coiled member has shape memory, and the inner coiled member has shape memory.

15. The syringe assembly according to claim 1, wherein the head of the plunger and the inner plug seal the first chamber from the second chamber, the inner plug and the outer plug seal the second chamber from the first chamber and from the third chamber, all before the plunger is moved from the initial position of the head toward the second position of the head.

16. A syringe assembly, comprising:
a barrel, the barrel is arranged about a longitudinal axis and is fitted internally with a plug and a framework each arranged about the longitudinal axis of the barrel, the plug is engaged slidably to the barrel, a chamber in the barrel is between an outer plug and a discharge end of the barrel, and the framework is collapsible and is in a chamber; and
the plug slides along the barrel and moves through the chamber collapsing the framework between the outer plug and the discharge end of the barrel for turbulent mixing a first component and a second component in the chamber into a solution, when the plug is plunged along the barrel toward the discharge end from a first position of the plug to a plunged position of the plug toward the discharge end;
wherein the first component is one of a solvent and a solute, and the second component is the other one of the solvent and the solute,
wherein the framework comprises coiled members, the coiled members are coiled helically in a longitudinal direction about the longitudinal axis of the barrel from an upper washer juxtaposed to the outer plug to a lower washer juxtaposed to the discharge end, wherein the outer plug drives the upper washer through the chamber toward the lower washer collapsing the coiled members therebetween, when the outer plug moves through the chamber when a plunger is plunged along the barrel from the second position of the head to the plunged position of the head.

17. The syringe assembly according to claim 16, wherein:
the plug includes a surface facing the chamber;
the upper washer comprises a disk-shaped plate having a central hole, an upper annular surface facing the second surface of the outer plug, a lower annular surface facing the discharge end, and a perimeter edge, the upper annular surface and the lower annular surface extend outwardly from the central hole to the perimeter edge juxtaposed to the barrel; and
the lower washer comprises a disk-shaped plate having a central hole, an upper annular surface facing the outer plug, a lower annular surface facing the discharge end, and a perimeter edge, the upper annular surface of the lower washer and the lower annular surface of the lower washer extend outwardly from the central hole of the lower washer to the perimeter edge of the lower washer juxtaposed to the barrel;
wherein the central hole of the upper washer enables first component and the second component to pass therethrough in the chamber to the coiled members, and the central hole of the lower washer enables the solution to pass therethrough from the coiled members to the discharge end of the barrel.

18. The syringe assembly according to claim 17, wherein the central hole of the upper washer and the central hole of the lower washer are coaxial with respect to the longitudinal axis of the barrel.

19. The syringe assembly according to claim 18, wherein the upper annular surface of the upper washer, the lower annular surface of the upper washer, the upper annular surface of the lower washer, and the lower annular surface of the lower washer are parallel relative to each other and to the second surface of the plug.

20. The syringe assembly according to claim 19, wherein the coiled members comprise:
an inner coiled member and an outer coiled member;
the inner coiled member includes an upper end and a lower end, and is coiled helically about the longitudinal axis of the barrel from the upper end of the inner coiled member connected to the lower annular surface of the upper washer to the lower end of the inner coiled member connected to the upper annular surface of the lower washer; and
the outer coiled member includes an upper end and a lower end, and is coiled helically about the longitudinal axis of the barrel and the inner coiled member from the an upper end of the outer coiled member connected to the lower annular surface of the upper washer to the lower end of the outer coiled member connected to the upper annular surface of the lower washer.

21. The syringe assembly according to claim 20, wherein:
the outer coiled member includes an inner edge, an outer edge, an upper surface, and a lower surface that together coil helically from the upper end of the outer coiled member connected to the lower annular surface of the upper washer to the lower end of the outer coiled member connected to the upper annular surface of the lower washer, the upper surface of the outer coiled member and the lower surface of the outer coiled member extend outwardly from the inner edge of the outer coiled member to the outer edge of the outer coiled member juxtaposed to the barrel; and
the inner coiled member includes an inner edge, an outer edge, an upper surface, and a lower surface that together coil helically from the upper end of the inner coiled member connected to the lower annular surface of the upper washer to the lower end of the inner coiled member connected to the upper annular surface of the lower washer, the upper surface of the inner coiled member and the lower surface of the inner coiled member extend outwardly from the inner edge of the inner coiled member to the outer edge of the inner coiled member between the barrel and the outer coiled member.

22. The syringe assembly according to claim 21, wherein the upper surface of the outer coiled member is flat and the lower surface of the outer coiled member is flat for enabling the upper surface of the outer coiled member and the lower surface of the outer coiled member to turbulent mix the first component and the second component in the chamber into the solution, when the outer coiled member collapses between the upper washer and the lower washer when the plug is plunged along the barrel toward the discharge end from the first position of the plug to the plunged position of the plug.

23. The syringe assembly according to claim 22, wherein the upper surface of the inner coiled member is flat and the lower surface of the inner coiled member is flat for enabling the upper surface of the inner coiled member and the lower surface of the inner coiled member to turbulent mix the first component and the second component in the chamber into the solution, when the outer coiled member collapses between the upper washer and the lower washer when the plug is plunged along the barrel toward the discharge end from the first position of the plug to the plunged position of the plug.

24. The syringe assembly according to claim 23, wherein:
the upper surface of the outer coiled member is parallel relative to the lower surface of the outer coiled member; and
the upper surface of the inner coiled member is parallel relative to the lower surface of the inner coiled member.

25. The syringe assembly according to claim 24, wherein the inner coiled member is formed with platforms, the platforms are spaced along the longitudinal axis of the barrel between the central hole of the upper washer and the central hole of the lower washer and cooperate with the inner coiled member and the outer coiled member to turbulent mix the first component and the second component in the chamber into the solution, when the inner coiled member and the outer coiled member collapse between the upper washer and the lower washer when the plug is plunged along the barrel toward the discharge end from the first position of the plug to the plunged position of the plug.

26. The syringe assembly according to claim 25, wherein the platforms extend inwardly from the inner edge of the inner coiled member under the central hole of the upper washer and over the central hole of the lower washer, and are parallel relative to each other.

27. The syringe assembly according to claim 26, wherein the platforms each include an upper surface facing and parallel to the lower annular surface of the upper washer and a lower surface facing and parallel to the upper annular surface of the lower washer.

28. The syringe assembly according to claim 27, wherein the outer coiled member has shape memory, and the inner coiled member has shape memory.

29. A syringe assembly, comprising:
a barrel, the barrel is arranged about a longitudinal axis and is fitted internally with an inner plug, an outer plug, and a framework each arranged about the longitudinal axis of the barrel, the inner plug and the outer plug are engaged slidably to the barrel, a first chamber in the barrel for containing a first component and a second component initially mixed therein is between the inner plug and the outer plug, a second chamber in the barrel is between the outer plug and a discharge end of the barrel, and the framework is collapsible and is in the second chamber;
the inner plug slides along the barrel and moves through the first chamber to against the outer plug for driving the first component and the second component from the first chamber between the barrel and the outer plug and into the second chamber, when the inner plug is plunged along the barrel toward the outer plug from a first position of the inner plug to a second position of the inner plug; and
the inner plug and the outer plug concurrently slide along the barrel and the outer plug moves through the second chamber collapsing the framework between the outer plug and the discharge end for turbulent mixing the first component and the second component in the second chamber into a solution and for injecting the solution through the discharge end of the barrel from the second chamber, when the inner plug is plunged along the barrel toward the discharge end from the second position of the inner plug to a plunged position of inner plug;
wherein the first component is one of a solvent and a solute, and the second component is the other one of the solvent and the solute.

30. The syringe assembly according to claim 29, wherein the framework comprises coiled members, the coiled members are coiled helically in a longitudinal direction about the longitudinal axis of the barrel from an upper washer juxtaposed to the outer plug to a lower washer juxtaposed to the discharge end, wherein the outer plug drives the upper washer through the second chamber toward the lower washer collapsing the coiled members therebetween, when the outer plug moves through the second chamber when the inner plug is plunged along the barrel from the second position of the inner plug to the plunged position of the inner plug.

31. The syringe assembly according to claim 30, wherein:
the outer plug includes a first surface facing the first chamber, and a second surface facing the second chamber;
the upper washer comprises a disk-shaped plate having a central hole, an upper annular surface facing the second surface of the outer plug, a lower annular surface facing the discharge end, and a perimeter edge, the upper annular surface and the lower annular surface extend outwardly from the central hole to the perimeter edge juxtaposed to the barrel; and
the lower washer comprises a disk-shaped plate having a central hole, an upper annular surface facing the outer plug, a lower annular surface facing the discharge end, and a perimeter edge, the upper annular surface of the lower washer and the lower annular surface of the lower washer extend outwardly from the central hole of the lower washer to the perimeter edge of the lower washer juxtaposed to the barrel;
wherein the central hole of the upper washer enables the first component and the second component to pass therethrough in the second chamber to the coiled members, and the central hole of the lower washer enables the solution to pass therethrough from the coiled members to the discharge end of the barrel.

32. The syringe assembly according to claim 31, wherein the central hole of the upper washer and the central hole of the lower washer are coaxial with respect to the longitudinal axis of the barrel.

33. The syringe assembly according to claim 32, wherein the upper annular surface of the upper washer, the lower annular surface of the upper washer, the upper annular surface of the lower washer, and the lower annular surface of the lower washer are parallel relative to each other and to the second surface of the outer plug.

34. The syringe assembly according to claim 33, wherein the coiled members comprise:
an inner coiled member and an outer coiled member;
the inner coiled member includes an upper end and a lower end, and is coiled helically about the longitudinal axis of the barrel from the upper end of the inner coiled member connected to the lower annular surface of the upper washer to the lower end of the inner coiled member connected to the upper annular surface of the lower washer; and
the outer coiled member includes an upper end and a lower end, and is coiled helically about the longitudinal axis of the barrel and the inner coiled member from the an upper end of the outer coiled member connected to the lower annular surface of the upper washer to the lower end of the outer coiled member connected to the upper annular surface of the lower washer.

35. The syringe assembly according to claim 34, wherein:
the outer coiled member includes an inner edge, an outer edge, an upper surface, and a lower surface that together coil helically from the upper end of the outer coiled member connected to the lower annular surface of the upper washer to the lower end of the outer coiled member connected to the upper annular surface of the lower washer, the upper surface of the outer coiled member and the lower surface of the outer coiled member extend outwardly from the inner edge of the outer coiled member to the outer edge of the outer coiled member juxtaposed to the barrel; and
the inner coiled member includes an inner edge, an outer edge, an upper surface, and a lower surface that together coil helically from the upper end of the inner coiled member connected to the lower annular surface of the upper washer to the lower end of the inner coiled member connected to the upper annular surface of the lower washer, the upper surface of the inner coiled member and the lower surface of the inner coiled member extend outwardly from the inner edge of the inner coiled member to the outer edge of the inner coiled member between the barrel and the outer coiled member.

36. The syringe assembly according to claim 35, wherein the upper surface of the outer coiled member is flat and the lower surface of the outer coiled member is flat for enabling the upper surface of the outer coiled member and the lower surface of the outer coiled member to turbulent mix the first component and the second component in the second chamber into the solution, when the outer coiled member collapses between the upper washer and the lower washer when the outer plug moves through the second chamber when the inner plug is plunged along the barrel from the second position of the inner plug to the plunged position of the inner plug.

37. The syringe assembly according to claim 36, wherein the upper surface of the inner coiled member is flat and the lower surface of the inner coiled member is flat for enabling the upper surface of the inner coiled member and the lower surface of the inner coiled member to turbulent mix the first component and the second component in the second chamber into the solution, when the inner coiled member collapses between the upper washer and the lower washer when the outer plug moves through the second chamber when the inner plug is plunged along the barrel from the second position of the inner plug to the plunged position of the inner plug.

38. The syringe assembly according to claim 37, wherein:
the upper surface of the outer coiled member is parallel relative to the lower surface of the outer coiled member; and
the upper surface of the inner coiled member is parallel relative to the lower surface of the inner coiled member.

39. The syringe assembly according to claim 38, wherein the inner coiled member is formed with platforms, the platforms are spaced along the longitudinal axis of the barrel between the central hole of the upper washer and the central hole of the lower washer and cooperate with the inner coiled member and the outer coiled member to turbulent mix the first component and the second component in the third second into the solution, when the inner coiled member collapses between the upper washer and the lower washer when the outer plug moves through the second chamber when the inner plug is plunged along the barrel from the second position of the inner plug to the plunged position of the inner plug.

40. The syringe assembly according to claim 39, wherein the platforms extend inwardly from the inner edge of the inner coiled member under the central hole of the upper washer and over the central hole of the lower washer, and are parallel relative to each other.

41. The syringe assembly according to claim 40, wherein the platforms each include an upper surface facing and parallel to the lower annular surface of the upper washer and a lower surface facing and parallel to the upper annular surface of the lower washer.

42. The syringe assembly according to claim 41, wherein the outer coiled member has shape memory, and the inner coiled member has shape memory.

* * * * *